(12) United States Patent
Yang et al.

(10) Patent No.: US 6,661,233 B2
(45) Date of Patent: Dec. 9, 2003

(54) GAS ANALYZER WITH REAL-TIME BROADBAND MONITORING AND SNAPSHOT SELECTIVE DETECTION

(75) Inventors: Wenjun Yang, San Jose, CA (US); Peter C. Hsi, Fremont, CA (US)

(73) Assignee: RAE Systems, Inc., Sunnyvale, CA (US)

( * ) Notice: Subject to any disclaimer, the term of this patent is extended or adjusted under 35 U.S.C. 154(b) by 67 days.

(21) Appl. No.: 09/978,260

(22) Filed: Oct. 15, 2001

(65) Prior Publication Data

US 2003/0071629 A1 Apr. 17, 2003

(51) Int. Cl.[7] .................. G01N 27/62; G01N 30/02; G01N 1/00
(52) U.S. Cl. ............... 324/464; 73/23.35; 73/23.41
(58) Field of Search ............... 324/464; 73/23.35, 73/23.36, 23.41, 23.42

(56) References Cited

U.S. PATENT DOCUMENTS

| | | | | |
|---|---|---|---|---|
| 3,847,546 A | * | 11/1974 | Paul ................... | 73/23.35 |
| 5,014,009 A | * | 5/1991 | Arimoto et al. .......... | 324/464 |
| 5,099,743 A | * | 3/1992 | Rounbehler et al. ...... | 73/23.41 |
| 5,265,031 A | * | 11/1993 | Malczewski ............ | 702/24 |
| 5,589,630 A | * | 12/1996 | Wiegand et al. ......... | 73/23.35 |
| 5,955,886 A | * | 9/1999 | Cohen et al. ........... | 324/464 |
| 6,134,944 A | * | 10/2000 | Yu et al. .............. | 73/23.35 |
| 6,333,632 B1 | * | 12/2001 | Yang et al. ............ | 324/464 |

\* cited by examiner

*Primary Examiner*—N. Le
*Assistant Examiner*—Timothy J. Dole
(74) *Attorney, Agent, or Firm*—David T. Millers

(57) ABSTRACT

A gas analysis system and method use foreground broadband gas monitoring and background selective gas analysis. The foreground broadband monitoring indicates concentrations of a class of chemicals or contaminants in a gas sample, provides real-time warnings of contaminants, and can activate the background selective analysis. Separate broadband detectors and gas analyzers can respectively perform broadband monitoring and selective analysis. To reduce system components, a broadband detector that performs broadband monitoring switches to measure concentrations of chemicals output from a separation device for the selective analysis.

22 Claims, 3 Drawing Sheets

GAS ANALYZER WITH REAL-TIME BROADBAND MONITORING AND SNAPSHOT SELECTIVE DETECTION

BACKGROUND

Many gas detectors, such as flame ionization detectors (FIDs), photo-ionization detector (PIDs), corona discharge ionization detectors (CDIDs), thermal conductivity detectors (TCDs), and low explosion limit (LEL) sensors are broadband detectors that identify the presence or amount of gases or chemical vapors in a particular class of chemicals. Generally, broadband detectors cannot distinguish between individual chemicals in the detected class. Broadband detectors thus measure the total concentration of all chemicals in the class but cannot precisely identify whether a specific chemical is present.

An advantage of these broadband gas detectors is that they generally require very little time before providing a measurement result. Accordingly, broadband gas detectors can perform real-time monitoring that alerts a user when exposure to the detected class of chemicals occurs.

A disadvantage of broadband gas detectors is that the detected class of chemicals may include individual chemicals that are of more concern than other chemicals in the class. When the broadband gas detector indicates the presence or a total concentration of the detected class of chemicals, the broadband detector fails to indicate whether any of the detected gases is the one of most concern.

Another class of gas monitor uses selective detection technologies that sense only a particular substance. Carbon monoxide sensors, carbon dioxide sensors, hydrogen sulfide sensors, and oxygen sensors are a few are examples of sensors using selective detection technology. The selective detection technologies in these detectors target one particular chemical and do not need to separate different substances for separate measurements. Accordingly, these singles substance detectors can achieve real-time detection of a particular chemical but are little or no use for detection of other chemicals.

In some applications, detection of a class of chemicals or a single particular chemical is insufficient, and a gas sample needs to be analyzed to determine exactly which contaminants are present. Short of using an array or single substance detectors, which can be expensive and may miss some contaminants, analysis of a gas sample requires a device that separates the individual chemicals for separate measurements. Such separations take time, and current gas analyzers cannot achieve real-time analysis. For example, gas chromatographs, which are commonly used gas analyzers, are not real-time devices because column separation times for gas chromatographs are typically on the order of minutes.

The time delay for gas analysis has disadvantages. In particular, using a gas analyzer to detect contaminants in the surroundings might expose a user to contaminants for several minutes before the analysis results indicated the contaminants were present. Alternatively, a user waiting for analysis results before risking exposure wastes time and resources when the results of the gas analysis indicate that no contaminants of concern are present.

Another disadvantage of gas analyzers is that the user must select when and where to activate the gas analyzer to begin analysis. Accordingly, a user may not make effective use of the gas analyzer to test conditions at places and times when contaminants are most likely to be present. Alternatively, frequent tests that mostly provide negative results waste time and shorten the useful life of the gas analyzer.

In view of the drawbacks of current gas detectors and analyzers, a gas analysis system is desired that avoids or minimizes wasted time for negative results and provides real-time exposure alerts.

SUMMARY

In accordance with an aspect of the invention, a gas analysis system includes a broadband gas detector and a gas analyzer. The broadband detector operates in the foreground to provide a user with real-time measurements of gas contaminants and real-time alerts if measured contaminant levels are high. The broadband detector can also trigger the gas analyzer to begin measurement of the specific constituents of the detected contaminants. The gas analyzer when triggered operates in the background and analyzes a snapshot sample of the contaminants that the broadband detector detected. Accordingly, the broadband detector helps the user avoid exposure to contaminants, and the gas analysis is strategically activated when the surroundings contain something to be analyzed.

A system with real-time broadband detection and triggered gas analysis has many advantageous over current gas analysis systems. In particular, the system can provide real-time broadband gas monitoring with the capability of selective gas analysis when analysis is required or desired. The broadband gas monitoring gives the user fast qualitative warnings and quantitative measurements, while the selective analysis provides more detailed and targeted quantitative analysis of the contaminants. Both broadband detections and selective analysis can operate in parallel without interrupting or hampering the operation of the other. Since the gas analyzer is triggered only when there is something to measure, unnecessary analysis is avoided, which can save the user time, conserve battery power in portable applications, and extend the useful life of the gas analyzer.

One specific embodiment of the invention is gas analysis system that includes a gas analyzer and a broadband gas detector. The broadband gas detector, which can be an FID, PID, CDID, TCD, LEL sensor, or a similar device, activates the gas analyzer in response to detecting total concentration above a threshold level. The gas analyzer once activated analyzes a gas sample to identify specific constituents.

The gas analyzer typically includes a separation device such as a capillary gas chromatographic column and may include a detector for the outflow from the separation device. When the gas analyzer includes a detector, the gas analyzer can perform selective detection while the broadband gas detector simultaneously performs broadband detection.

If the gas analyzer does not include a detector, output gases from the separation device can be directed to the broadband detector, which then detects concentrations of separated chemicals as the chemicals sequentially leave the separation device. A gas flow system connected to the broadband detector can operate in a broadband mode that bypasses the separation device when directing gas to the broadband detector and a selective mode that directs gas output from the separation device to the broadband detector for measurement.

Another embodiment of the invention is gas analysis system that includes a broadband detector, a molecular separation device, and a multimode gas flow system. The gas flow system operates in a broadband mode that bypasses the separation device when directing gas to the broadband detector and a selective mode that directs gas output from the separation device to the broadband detector.

Yet another embodiment of the invention is a gas analysis process that includes operating a broadband detector to perform real-time, broadband detection of a class of chemicals in gas flow. In response to the broadband detection indicating a concentration above a threshold level, a gas analyzer performs selective detections of specific chemicals in a snapshot sample of gas that the broadband detection indicated had the concentration above the threshold level. The broadband detection and selective detection can be performed in parallel, or broadband detection can be suspended during all or a portion of the time during which selective detection is performed.

BRIEF DESCRIPTION OF THE DRAWINGS

Use of the same reference symbols in different figures indicates similar or identical items.

DETAILED DESCRIPTION

In accordance with an aspect of the invention, a gas analyzer provides two parallel detection modes. One mode is foreground real-time broadband monitoring, and the other is background selective detection or analysis. The real-time monitoring determines whether chemicals in a class of concern are present, measures the amount or concentration of those chemicals, and activates an alarm according to a user-set threshold. When the concentration of the detected class of chemicals reaches the same or another user-set threshold, the foreground broadband detection either automatically triggers the background gas analysis or alerts the user to activate the background gas analysis. The background gas analysis selectively analyzes a gas sample for targeted components and determines individual amounts for the targeted components. During the background gas analysis, the broadband detection can continue in the foreground or can be suspended.

The system effectively takes snapshots of gas or environmental conditions when substances of concern are present. The snapshots can be automatically or manually marked according to the time, location, or any other practical identifier, and after a period of time, the snapshots can be analyzed to determine correlations. In particular, an embodiment of the invention that has a fixed location can provide a precise history of the levels of specific contaminants without requiring frequent operation of the gas analyzer when contaminants are not present. In a portable application, the locations and composition of specific contaminants can be mapped again without the need for frequent operation of the gas analyzer when there is nothing of interest to analyze. Since the gas analyzer operates only when contaminants are present, the useful life of the gas analyzer can be extended and power consumption can be reduced, which is particularly important in portable applications.

Figure 1:
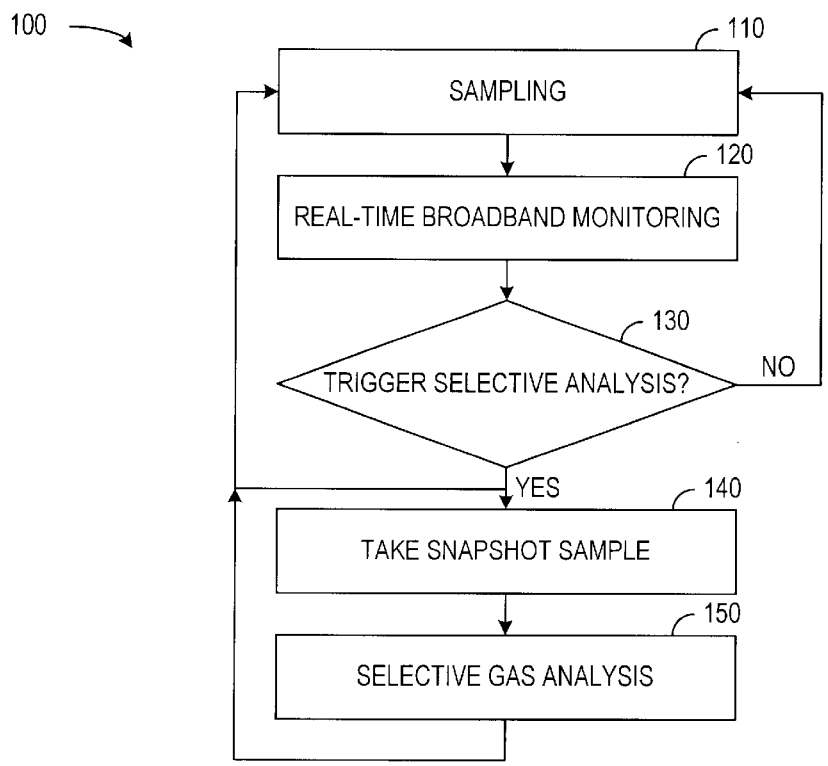
FIG. 1 is a flow diagram of a gas monitoring and analysis process in accordance with an embodiment of the invention.

FIG. 1 is a flow diagram illustrating a measurement process 100 that combines gas analysis with broadband detection in accordance with an embodiment of the invention. For process 100, sampling 110 draws sample gases from the surrounding atmosphere for detection and possible analysis. In particular, broadband monitoring 120 using a conventional broad detector detects the amount or concentration of a detected class of chemicals in a sample. The broadband detector can be, for example, a flame ionization detector (FID), a photo-ionization detector (PID), a corona discharge ionization detector (CDID), a thermal conductivity detector (TCD), low explosion limit (LEL) sensor, or another measurement device that detects a class of chemicals such as gases having ionization energies below a selected limit.

Sampling 110 and broadband monitoring 120 are processes that continuously sample and monitor the surrounding atmosphere for the detected class of chemicals. Additionally, broadband monitoring 120 is a real-time process so that detection or measurement of a concentration of the detected class of chemicals occurs when the chemicals are present in the detector.

If the measured concentration of the class of chemicals detected rises above a threshold level, step 130 triggers selective analysis. The selective analysis begins in step 140 by taking a snapshot sample of the surrounding atmosphere. The snapshot sample includes the contaminants that broadband monitoring 120 found at a concentration above the threshold level. Selective analysis in step 150 can proceed in the background while sampling 110 and broadband monitoring 120 continue in the foreground.

Selective gas analysis 150 does not need to be a real-time analysis because the broadband monitoring 120 gives the user immediate warnings. Accordingly, selective gas analysis 150 can use a molecular separation technique such as used in a gas chromatograph or an ion separation technique such as used in a mass spectrometer or an ion mobility spectrometer. Gas analysis can take up to several minutes to provide a detailed analysis of which chemicals were present in the snapshot sample.

Figure 2:
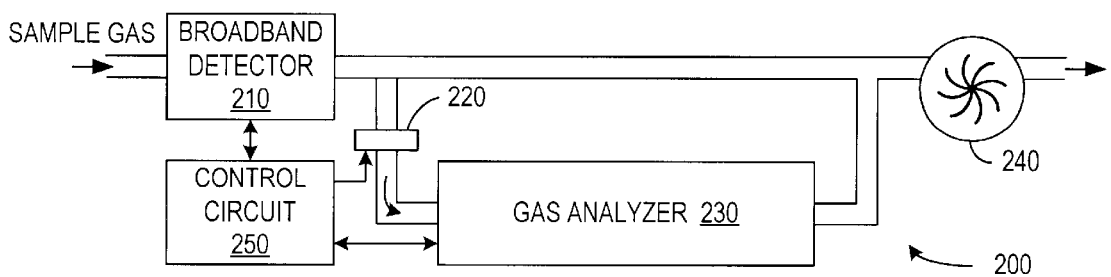
FIG. 2 is a block diagram of a gas monitor and analyzer system in accordance with an embodiment of the present invention.

FIG. 2 is a block diagram of a gas analysis system 200 in accordance with an embodiment of the invention. Gas analysis system 200 includes a broadband detector 210, a control valve 220, a gas analyzer 230, a pump 240, and a control circuit 250.

Broadband detector 210 can be a FID, PID, CDID, TCD, LEL, or any other broadband detector capable of real-time detection of a desired class of chemicals such as volatile gases.

Figure 3:
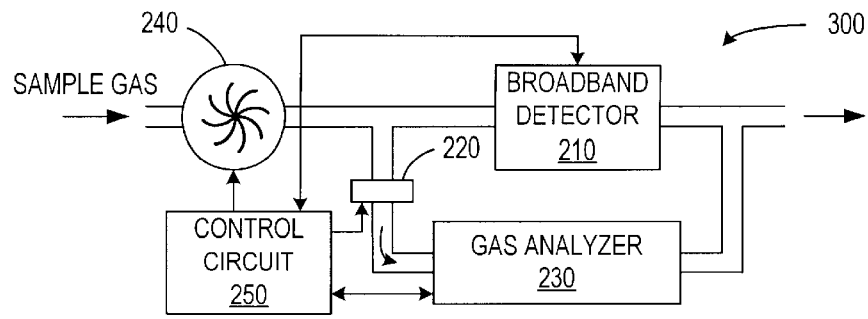
FIG. 3 is a block diagram of a gas monitor and analyzer system having an alternative gas flow in accordance with an embodiment of the present invention.

Control valve 220 and pump 240 are parts of a gas flow system that delivers sample gas to broadband detector 210 and gas analyzer 230 for measurements. The configuration of the gas flow system and particularly the connections of gas inlets, outlets, lines, and pumps are subject to variation in keeping with the invention. For example, broadband detector 210 and gas analyzer 230 can have inlets connected to the same input line or different input lines. Similarly, outlets of detector 210 and gas analyzer 230 can be connected to the same or different lines, and pump 240 can be positioned almost anywhere in the gas flow system. FIG. 3 shows a gas analysis system 300 with broadband detector 210 and pump 240 in alternative positions in the gas flow system.

During operation of the gas flow system, pump 240 draws or pushes a continuous gas flow through broadband detector 210, and broadband detector outputs a measurement signal indicating the total concentration of gases in the detected class.

Control circuit 250, which receives the measurement signal from broadband detector 210, can include a microprocessor or microcontroller that executes software or firmware that responds according to the level of the measurement signal. In particular, control circuit 250 can control a user interface such as an LED display, an alarm indicator, and a user operated control to display the measured concentration of the detected class of gases or chemical vapors, to indicate a warning if the measured concentration rises above a threshold level, and to receive a user's input for further control of gas analysis system 200.

Control circuit 250 also operates valve 220, which is in an inlet line to gas analyzer 230. When the measurement signal from broadband detector 210 indicates a contaminant concentration above a threshold level or when user directs system 200 to begin gas analysis, control circuit 250 briefly opens valve 220 to introduce a snapshot sample into gas analyzer 230 for analysis. When detection of high broadband concentrations triggers gas analysis, the real-time broadband detection allows taking of the snapshot sample contemporaneously with the detection of high broadband levels.

Gas analyzer 230 can employ any of a variety of techniques for analysis of the constituent contaminants in the sample gas. For example, gas analyzer 230 can use molecular or ion separation such as in a gas chromatograph, an ion mobility spectrometer, or mass spectrometer. Alternatively, gas analyzer can include one or more chemical specific sensors (e.g., carbon monoxide, carbon dioxide, oxygen, ammonia, or hydrogen sulfide sensors).

Figure 4:
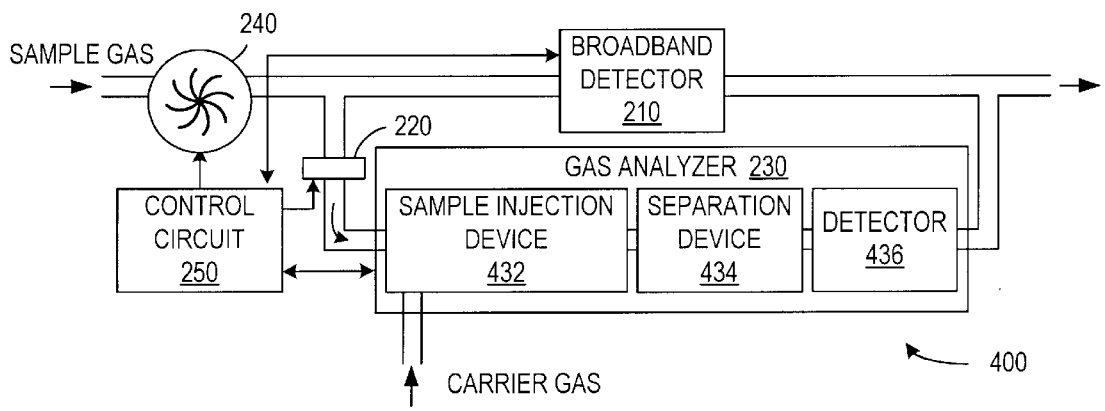
FIG. 4 is a block diagram of a gas monitor and analyzer system using molecular separation for gas analysis in accordance with an embodiment of the present invention.

FIG. 4 shows a gas analysis system 400 in which gas analyzer 230 uses molecular separation in analyzing the constituents of the sample gas. Gas analysis system 400 is otherwise substantially the same as gas analysis systems 200 and 300 described above, except that gas analyzer 230 in system 400 is specific. In system 400, gas analyzer 230 includes a sample injection system 432, a separation device 434, and a detector 436.

Sample injection system 432 receives the snapshot sample when valve 220 is opened and provides a flow of carrier gas such as an inert gas, nitrogen, or zero air that carries the snapshot sample through the separation device 434. Such injection systems are conventional for analyzers such as gas chromatographs.

Separation device 434 separates the contaminants in the snapshot sample so that different chemicals leave separation device 434 at different times. Separation device 434 can be a gas chromatographic column such as a 4 m×0.25 mm×1.20 µm capillary gas chromatographic column.

Detector 436 detects the concentrations of each chemical as the chemicals leave separation device 434, and control circuit 250 can identify the concentrations of specific chemicals from the time between introduction of the snapshot sample and the concentration measurement. Such separation techniques generally require a few minutes with current gas chromatographs.

Figure 5:
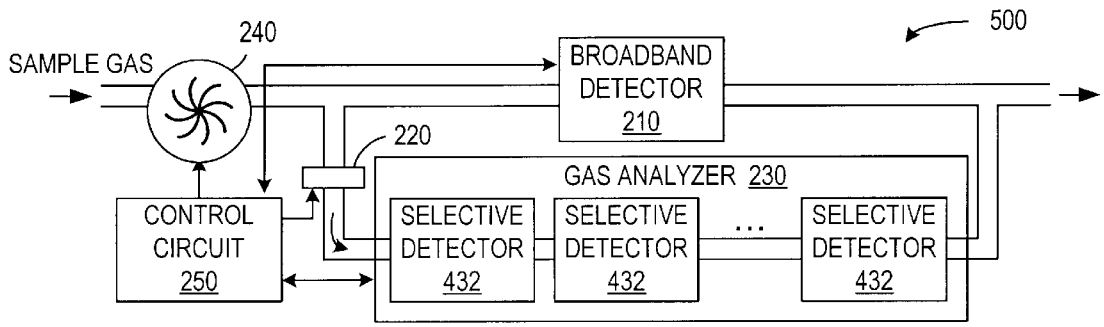
FIG. 5 is a block diagram of a gas monitor and analyzer system using one or more selective detectors for gas analysis in accordance with an embodiment of the present invention.

FIG. 5 shows a gas monitoring and analysis system 500 in which gas analyzer 230 includes a set of one or more selective detectors 432. In illustrated embodiment, selective detectors 432 are arranged sequentially along the gas flow, but other configurations such as parallel gas flows are also suitable. Generally, each selective detector 432 measures the concentration of a different chemical and sends a measurement signal to control circuit 250 for user access. Although chemical specific sensors 432 may be fast enough for real-time detection, use of broadband detector 210 to trigger operation of gas analyzer 230 and chemical specific sensors 432 only when contaminants are present reduces power consumption and extends the useful life of the selective detectors 432.

Figure 6:
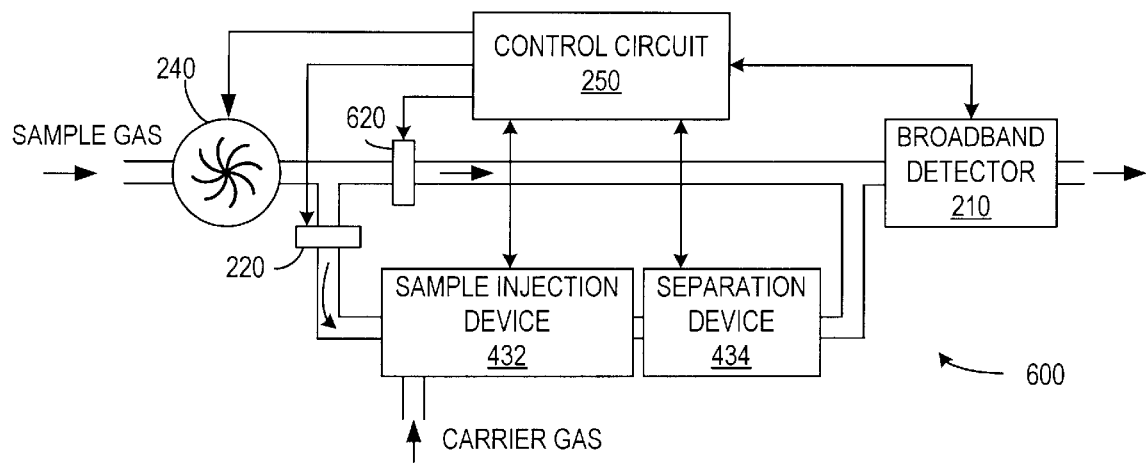
FIG. 6 is a block diagram of a gas monitor and analyzer system using the same detector for broadband detection and gas analysis in accordance with an embodiment of the present invention.

FIG. 6 is a block diagram of a gas monitoring and analysis system 600 in accordance with another embodiment of the invention. System 600 includes a broadband detector 210, gas flow valves 220 and 620, a separation device 434, a pump 240, and a control circuit 250. Gas analyzer 600 differs from gas monitoring and analysis system 400 predominantly in that broadband detector 210 is used both for broadband detection and for selective analysis.

During operation of gas analyzer 600, pump 240 normally draws gas from the surroundings through valve 620, and broadband detector 210 monitors the total concentration of chemicals in the detected class.

When broadband detector 210 detects a contaminant concentration above a threshold level, control circuit 250, which receives the measurement signal from broadband detector 210 briefly opens valve 220 to introduce a snapshot sample into sample injection device 432. Sample injection device 432 that provides a carrier gas that carries the snapshot sample through separation device 434. As the contaminants in the snapshot sample filter through separation device 434, broadband detector 210 detects the concentrations of the separated contaminants that leave separation device 434 at different times. Accordingly, system 600 does not require the detector 436 used in system 400, and system 600 may provide a lower cost and easier-to-operate gas analysis system.

Control circuit 250 shuts of valve 620 to suspend gas flow and broadband detection that may interfere with measurements that detector 210 performs for gas analysis. One operation technique suspends broadband detection from the time of taking of the snapshot sample until gas analysis is complete. Alternatively, control circuit 250 can operate valve 620 to suspend broadband sensing only when the broadband sensing interferes with measurement of specific chemicals leaving separation device 434. In particular, knowing the propagation times through separation device 434 for specific chemicals of interest, control circuit 250 can shut off valve 620 during periods corresponding to the emergence of chemicals of interest from separation device 434, and open valve 620 for broadband sensing at other times.

A user of the gas detectors and analysis processes described above can depend on the broadband monitoring for real-time alerts or warnings about contaminant levels. When a warning occurs, the gas analysis within up to few minutes provides the user with detailed analysis of chemicals that caused the warning. Meanwhile, the on-going broadband survey can still be processed without being hampered by the background detailed analysis. The user can thus decide on an appropriate action with a minimum of delay. Additionally, the sensitive and less durable separation components of the gas analysis systems are used only when positive analysis results are likely, which can save power and extend the useful life of the separation components.

Although the invention has been described with reference to particular embodiments, the description is only an example of the invention's application and should not be taken as a limitation. Various adaptations and combinations of features of the embodiments disclosed are within the scope of the invention as defined by the following claims.

What is claimed is:

1. A gas analysis system comprising:

a gas analyzer; and a broadband gas detector connected to activate the gas analyzer, wherein in response to the broadband gas detector detecting a concentration above a threshold level, the gas analyzer is activated, and in response to the broadband gas detector detecting that the concentration is below the threshold level, the gas analyzer is not activated.

2. The system of claim 1, wherein the gas analyzer once activated analyzes a gas sample to identify specific constituents while the broadband gas detector simultaneously performs broadband sensing of a class of chemical.

3. The system of claim 1, wherein the gas analyzer comprises a separation device.

4. The system of claim 3, further comprising a gas flow system connected to the broadband detector, wherein the gas flow system is operable in a first mode that bypasses the separation device when directing gas to the broadband detector for measurement and a second mode that directs gas output from the separation device to the broadband detector for measurement.

5. The system of claim 3, wherein the separation device comprises a molecular separation column.

6. The system of claim 5, wherein the molecular separation column comprises a gas chromatographic column.

7. The system of claim 1, wherein the gas analyzer comprises an ion separation and detection device.

8. The system of claim 7, wherein the ion separation device comprises an ion mobility spectrometer.

9. The system of claim 7, wherein the ion separation device comprises a mass spectrometer.

10. The system of claim 1, wherein the gas analyzer comprises a chemical specific sensor.

11. The system of claim 1, wherein the gas analyzer comprises a plurality of chemical specific sensors.

12. A gas analysis system comprising:

a broadband detector;

a separation device;

a gas flow system connected to the broadband detector, wherein the gas flow system is operable in a first mode that bypasses the separation device when directing gas to the broadband detector for measurement and a second mode that directs gas output from the separation device to the broadband detector for measurement.

13. The system of claim 12, further comprising a control circuit connected to the broadband detector and the gas flow system, wherein the control circuit responds to the broadband detector indicating that gas measured contains a concentration above a threshold level by introducing a gas sample into the separation device.

14. The system of claim 13, wherein after the introduction of the gas sample to the separation device, the control circuit sets the gas flow system to the second mode during periods corresponding to selected chemicals from the gas sample leaving the separation device.

15. The system of claim 14, wherein the control circuit switches the gas flow system from operating in the second mode to operating in the first mode during intervals between the periods corresponding to the selected chemicals leaving the separation device.

16. The system of claim 12, wherein the separation device comprises a molecular separation column.

17. A gas sensing process comprising:

operating a broadband detector to perform real-time, broadband detection of a class of chemicals in a gas flow; and in response to the broadband detection indicating a concentration above a threshold level, activating a gas analyzer to perform selective detections of specific chemicals of a snapshot sample of gas that the broadband detection indicated had the concentration above the threshold level.

18. The process of claim 17, wherein the broadband detection and selective detection are performed in parallel.

19. The process of claim 17, wherein:

the gas analyzer comprises a separation device; and activating the gas analyzer comprises introducing a snapshot sample into the separation device.

20. The process of claim 19, further comprising switching the broadband detector from performing broadband detection to detection of chemicals output from the separation device.

21. A gas analysis system comprising:

a gas detector capable of real-time sensing of a concentration of a class of chemicals in a gas flow;

a gas analyzer that when activated analyzes a gas sample to identify specific constituents that are in the class of chemicals; and a control circuit connected to the gas detector and the gas analyzer, wherein the control circuit determines whether or not to activate the gas analyzer based on whether or not the concentration that the gas detector senses is above or below a threshold level.

22. The system of claim 21, further comprising a gas flow system that operates to provide the gas flow to the gas detector and the gas sample to the gas analyzer, wherein the control circuit controls the gas flow system to direct output gas from the gas analyzer to the gas detector after activating the gas analyzer.

* * * * *